United States Patent
Campbell, Sr.

(10) Patent No.: US 6,629,532 B2
(45) Date of Patent: Oct. 7, 2003

(54) OXYGEN MASK RETENTION DEVICE AND METHOD FOR RETAINING AN OXYGEN MASK

(76) Inventor: George L. Campbell, Sr., 1011 E. Tonopah Dr., Phoenix, AZ (US) 85024

( * ) Notice: Subject to any disclaimer, the term of this patent is extended or adjusted under 35 U.S.C. 154(b) by 0 days.

(21) Appl. No.: 10/166,753

(22) Filed: Jun. 12, 2002

(65) Prior Publication Data

US 2003/0150459 A1 Aug. 14, 2003

Related U.S. Application Data

(60) Provisional application No. 60/354,484, filed on Feb. 8, 2002.

(51) Int. Cl.[7] ............................................. A62B 18/08
(52) U.S. Cl. ............................. 128/207.11; 128/206.13; 128/206.27
(58) Field of Search ................... 128/201.22, 201.23, 128/206.13, 206.27, 207.11, 207.17, DIG. 26, 205.25, 206.12, 206.18, 206.21, 206.28, 207.13

(56) References Cited

U.S. PATENT DOCUMENTS

| | | | | | |
|---|---|---|---|---|---|
| 1,297,337 | A | * | 3/1919 | Feltner | 128/206.27 |
| 2,176,709 | A | * | 10/1939 | Dym | 128/207.11 |
| 2,248,477 | A | * | 7/1941 | Lombard | 128/207.11 |
| 2,353,643 | A | * | 7/1944 | Bulbulian | 128/207.11 |
| 2,954,027 | A | * | 9/1960 | Marasco | 128/206.13 |
| 3,013,556 | A | * | 12/1961 | Galleher, Jr. | 128/207.11 |
| 3,713,448 | A | * | 1/1973 | Arrot | 128/207.17 |
| 4,201,205 | A | * | 5/1980 | Bartholomew | 128/205.25 |
| 4,878,491 | A | * | 11/1989 | McGilvray, III | 128/201.11 |
| 5,237,986 | A | * | 8/1993 | Seppala et al. | 128/201.23 |
| 5,400,776 | A | * | 3/1995 | Bartholomew | 128/200.24 |
| 5,533,506 | A | * | 7/1996 | Wood | 128/207.18 |
| 5,819,731 | A | * | 10/1998 | Dyrud et al. | 128/206.27 |
| 5,857,460 | A | * | 1/1999 | Popitz | 128/206.21 |
| 6,044,844 | A | * | 4/2000 | Kwok et al. | 128/207.11 |
| 6,338,342 | B1 | * | 1/2002 | Fecteau et al. | 128/207.11 |

* cited by examiner

Primary Examiner—Weilun Lo
Assistant Examiner—Joseph F. Weiss, Jr.
(74) Attorney, Agent, or Firm—Jeffrey Weiss; Harry M. Weiss; Weiss, Moy & Harris, P.C.

(57) ABSTRACT

A retention device and method for retaining an object, including preferably a gas mask, in position proximate a user's mouth. The retention device includes straps coupled to both sides of the object and having at ends thereof ear pieces. The ear pieces fit over the ears, and are configured to receive the strap at a point proximate the anterior, center portion of the ear, causing pulling forces to be on the posterior center portion of the ear rather than on the top of the ear.

1 Claim, 1 Drawing Sheet

OXYGEN MASK RETENTION DEVICE AND METHOD FOR RETAINING AN OXYGEN MASK

RELATED APPLICATION

This non-provisional application claims priority from provisional application No. 60/354,484, filed on Feb. 8, 2002.

BACKGROUND OF THE INVENTION

1. Field of the Invention

The present invention relates generally to medical devices, and more specifically, to a device and method for retaining a gas delivery system on the head of a recipient of a gas, particularly in trauma situations.

2. Background of the Invention

It is often necessary to supply oxygen or a gas mixture to a hospitalized patient or to an individual requiring supplemental assistance with breathing or who is subjected to a low-oxygen environment. This occurs, frequently, in trauma situations.

Often, in a trauma situation, an oxygen mask having a gas supply received through a bottom portion thereof will be utilized to deliver gas to the patient. In such instance, the mask is typically fitted with an elastic strap, which is intended to be fitted above the ears and around the back of the head of the individual who is to be receive the gas. However, this requires the lifting of the head of the individual, which in a trauma situation can be difficult or undesired.

Therefore, it is desirable to provide a device and method that will permit effective retention of a mask in a trauma situation without the necessity of lifting the head of the patient to position the mask.

SUMMARY OF THE INVENTION

It is an object of the present invention to provide a device and method that will permit effective retention of a mask in a trauma situation.

It is a further object of the present invention to provide a device and method that will permit effective retention of a mask in a trauma situation, and that does not require the lifting of the head of the patient to position the mask.

It is a still further object of the present invention to provide a retention device and method that will locate the pulling force on the mask proximate the center portion of the ear.

BRIEF DESCRIPTION OF THE PREFERRED EMBODIMENTS

In accordance with one embodiment of the present invention, a gas retention device is disclosed. The device comprises, in combination: an object to be positioned proximate a mouth of a user; a first strap coupled to a first side of the object and extending toward one of the user's ears; a second strap coupled to a second side of the object and extending toward another of the user's ears; a first ear piece coupled to the first strap; and a second ear piece coupled to the second strap; wherein each of the first ear piece and the second ear piece is coupled to a corresponding strap at a point proximate a corresponding anterior, central portion of the user's ear; wherein each of the first ear piece and the second ear piece is sufficiently rigid to transfer tension exerted by the object to a back of the user's ears.

In accordance with another embodiment of the present invention, a retention device is disclosed. The retention device comprises, in combination: an object to be positioned proximate a mouth of a user; wherein the object is a gas mask; a first strap coupled to a first side of the gas mask and extending toward one of the user's ears; a second strap coupled to a second side of the gas mask and extending toward another of the user's ears; wherein each of the first strap and the second strap is elastic; a first ear piece coupled to the first strap; and a second ear piece coupled to the second strap; wherein each of the first ear piece and the second ear piece is coupled to a corresponding strap at a point proximate a corresponding anterior, central portion of the user's ear; wherein each of the first ear piece and the second ear piece is sufficiently rigid to transfer tension exerted by the object to a back of the user's ears; and wherein each of the first ear piece and the second ear piece comprises a plastic material.

In accordance with yet another embodiment of the present invention, a method for retaining an object proximate a user's mouth is disclosed. The method comprises the steps of: providing an object to be positioned proximate a mouth of a user; providing a first strap coupled to a first side of the object and extending toward one of the user's ears; providing a second strap coupled to a second side of the object and extending toward another of the user's ears; providing a first ear piece coupled to the first strap; providing a second ear piece coupled to the second strap; wherein each of the first ear piece and the second ear piece is coupled to a corresponding strap at a point proximate a corresponding anterior, central portion of one of the user's ears; wherein each of the first ear piece and the second ear piece is sufficiently rigid to transfer tension exerted by the object to a back of the user's ears; positioning the object to proximate the mouth of the user; positioning the first ear piece over the one the ear of the user; and positioning the second ear piece over the other the ear of the user.

DETAILED DESCRIPTION OF THE PREFERRED EMBODIMENTS

Figure 1:
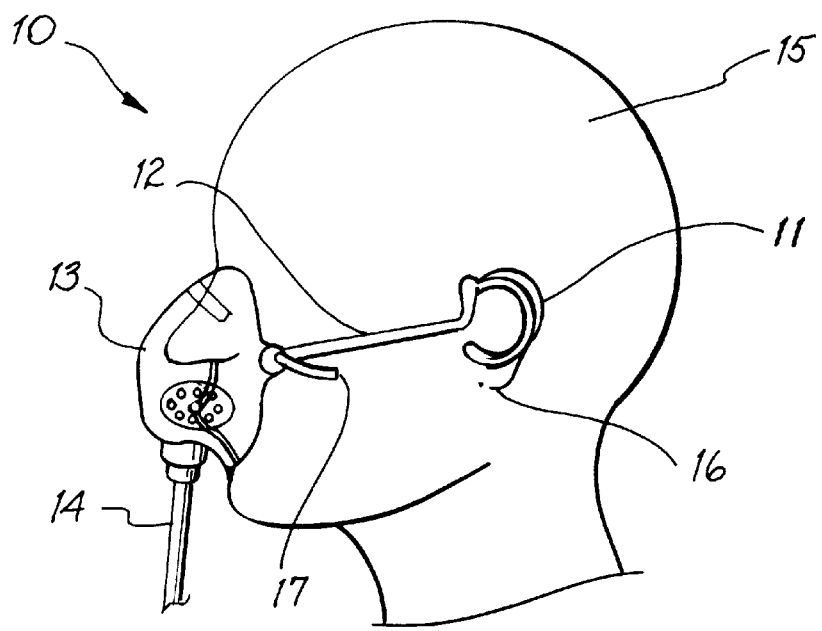
FIG. 1 is a side view showing an oxygen mask retention system according to the present invention.

Referring first to FIG. 1, an embodiment of an oxygen mask retention system 10 according to the present invention is shown. The oxygen mask retention system 10 generally comprises an oxygen mask retention device 11, two elastic straps 12 (the one on the other side of a recipient's head 15 is not shown), an oxygen mask 13, and a gas supply tube 14. The oxygen mask 13 receives its gas supply through a bottom portion thereof, through the gas supply tube 14.

Preferably, each elastic strap 12 is secured at a first end to a side of the oxygen mask 13, preferably in an adjustable manner. Such adjustment is provided by passing the elastic strap 12 in the direction of the oxygen mask 13 through a first slot on a side of the oxygen mask 13, and then pulling the elastic strap 12 in the direction of the oxygen mask retention device 11 through a second slot on the side of the oxygen mask 13. This will leave a free end 17 of elastic strap 12 exposed. To tighten the oxygen mask 13, the user will pull on the free end 17 after the oxygen mask retention device 11 and oxygen mask 13 are in place. To loosen the oxygen mask 13, the user will pull on the elastic strap 12 in the direction of the oxygen mask retention device 11.

The oxygen mask retention device 11 is secured to a second end of each elastic strap 12, and positioned on each of the recipient's ears 16 to secure the oxygen mask 13 in position on the recipient's head 15. (It should be noted that it would be possible to provide an adjustable coupling of the elastic strap 12 to the oxygen mask retention device 11, either in place of or in addition to the adjustable coupling provided at the sides of the oxygen mask 13.

Figure 2:
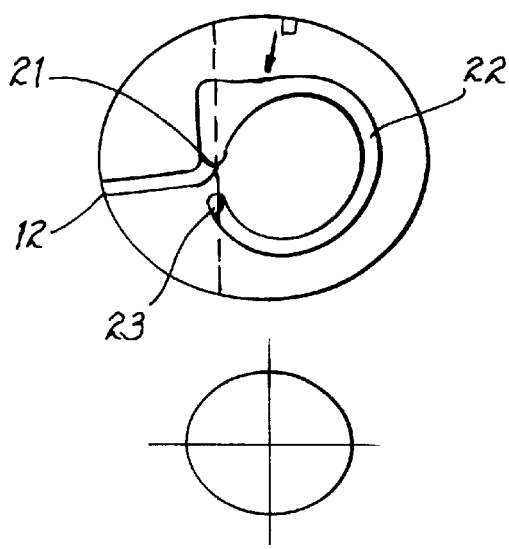
FIG. 2 is a side view showing the ear piece portion of an embodiment of the oxygen mask retention system of the present invention, prior to placement on a recipient's ear.
Figure 3:
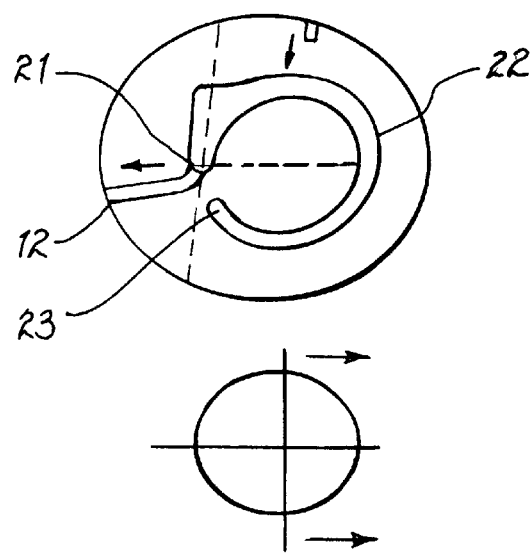
FIG. 3 is a side view showing the ear piece portion of an embodiment of the oxygen mask retention system of the present invention, in place on a recipient's ear, and the pulling forces thereon.

Now referring to FIGS. 2 and 3, the oxygen mask retention device 11 includes an ear piece 22 coupled at a point 21 to the elastic strap 12 at one end. The ear piece 22 is curved, to conform to the curvature of the recipient's ear 16. Although not required, it is preferred to provide a bulbed area 23 at the open end of the ear piece 22 to reduce the sharpness and to thereby improve the comfort of the recipient.

As shown in detail in FIGS. 2 and 3, the configuration of the oxygen mask retention device 11 positions the elastic strap 12 proximate the front center of the recipient's ear 16, as opposed to the top as in a typical eye glass ear piece. As a result, as shown in FIG. 3, the forward pulling force when the ear piece 22 is in position is transferred directly behind the recipient's ear 16, as indicated by the horizontal dotted line and forward-indicating arrow, resulting in a more secure fit of the oxygen mask 13 to the recipient's head and a lower risk of dislodging the oxygen mask 13 accidentally.

The oxygen mask retention device 11 will preferably be molded out of the plastic material, though other materials may be utilized. The plastic material preferably used should be hypoallergenic and sufficiently rigid to permit the oxygen mask retention device 11 to transfer tension to the back of the recipient's ear 16, while permitting comfortable use with some flexure as will occur with movement of the recipient's head 15 and compression if the weight of recipient's head 15 rests on one of the recipient's ears 16. A thermoplastic elastomer material is preferred, though other materials may also be utilized.

The oxygen mask retention device 11 can be modified in size and shape to comfortably fit on different ear sizes, to accommodate adults, children, and infants.

The oxygen mask retention device 11 may be used in a particularly effective manner with trauma patients. The design of the oxygen mask retention device 11, as shown in FIG. 1, allows the recipient's head 15 to be left lying down, with the oxygen mask secured by positioning the retention device 11 over each of the recipient's ears 16. The types of trauma situations in which the oxygen mask retention device 11 might be used include the use by the military for battlefield casualties.

While the depictions of FIG. 1 are described as applying to an oxygen mask, it should be understood that the retention device of the present invention is suitable for use with other gases and with other delivery systems, as well as filters and other breathing apparatus. The invention may also be applied to securing other devices to a patient's head, such as securing dental bridgework during and after installation. In such embodiments, it may be necessary, for example, to form the elastic straps 12 from a rigid, non-elastic material to provide stronger support. The elastic straps 12 could be, for example, a cannula. The term "strap" as used herein is intended to include both elastic and non-elastic versions.

While the invention has been particularly shown and described with reference to the preferred embodiments thereof, it will be understood by those skilled in the art that the foregoing and other changes in form, and details may be made therein without departing from the spirit and scope of the invention.

I claim:

1. A retention system comprising:

a respiratory appliance adapted to engage a patient in an oro-nasal area;

first and second flexible, elastic straps having first and second ends, said first ends of said first and second straps coupled to opposing sides of said respiratory appliance;

said first and second straps being sufficiently flexible and elastic for rapid and easy tension adjustment permitting optimal fit and comfort of said respiratory appliance to a patient;

wherein said first ends of said straps are adjustably coupled to said opposing sides of said respiratory appliance to permit easy access for adjustment by medical personnel;

first and second ear pieces adapted to engage a superior and posterior region of an auricle for optimal fit and comfort;

said first and second ear pieces being integrated into said second ends of said first and second straps at a strap coupling point;

said strap coupling point adapted to engage a region anterior to an auricle and adjacent to an auricle's tragus;

wherein said retention system is configured to permit rapid attachment and adjustment of said respiratory appliance to a patient without moving a patient's head and neck to minimize aggravating any injury to a patient.

* * * * *